United States Patent
Stroble et al.

(10) Patent No.: US 6,995,190 B2
(45) Date of Patent: Feb. 7, 2006

(54) METHOD AND TREATMENT WITH KETOPROFEN SOLUTION

(75) Inventors: Michael Stroble, Northfield, MN (US); Patrick Soderlund, New Prague, MN (US)

(73) Assignee: Veterinary Solutions, Northfield, MN (US)

( * ) Notice: Subject to any disclaimer, the term of this patent is extended or adjusted under 35 U.S.C. 154(b) by 0 days.

(21) Appl. No.: 09/801,908

(22) Filed: Mar. 9, 2001

(65) Prior Publication Data

US 2002/0169212 A1 Nov. 14, 2002

(51) Int. Cl.
A61K 31/19 (2006.01)

(52) U.S. Cl. .................................. 514/568
(58) Field of Classification Search ............. 514/570, 514/568
See application file for complete search history.

(56) References Cited

U.S. PATENT DOCUMENTS

| | | | | |
|---|---|---|---|---|
| 5,348,745 A | * | 9/1994 | Daher | 424/466 |
| 5,624,682 A | * | 4/1997 | Dondi et al. | 424/455 |
| 5,665,384 A | | 9/1997 | Courteille et al. | 424/451 |
| 5,900,416 A | * | 5/1999 | Markson | 424/728 |
| 6,069,172 A | | 5/2000 | Bertini et al. | 514/570 |

OTHER PUBLICATIONS

"In Greater Depth, Effervescent Technology Primer", http://www.phyzz.com/pdf/article.pdf, downloaded Nov. 24, 2003 at 12:59 pm EST.*

Higgins, A.J. et al., "Use of a novel non–steroidal anti–inflammatory drug in the horse," Equine vet. J. 19(t), pp. 60–66 (1987).

Julou, L. et al., "Main pharmacological properties: Outline of Toxicological and Pharmacokinetic Data," Scnd. J Rheumatology, Suppl. 14, pp. 33–42 (1976).

Longo, F. et al., "The effectiveness of Ketoprophene in the treatment of Equine Colic," Bull. Soc. Vet. Prat. de France, Jul. 1990, T. 74, No. 7, p. 377, pp. 1–2, 4–7, 10–15, (1990).

* cited by examiner

Primary Examiner—Raymond J. Henley, III
(74) Attorney, Agent, or Firm—Dechert, LLP; John W. Ryan

(57) ABSTRACT

A readily water-soluble ingestible form of ketoprofen is provided by the reaction of ketoprofen and any edible weak base to yield a palatable, stable, safe pharmaceutical solution for mass medication of animals. Any edible weak base such as sodium bicarbonate may be used with ketoprofen in a ratio of 10 to 1 by weight.

13 Claims, No Drawings

METHOD AND TREATMENT WITH KETOPROFEN SOLUTION

FIELD OF THE INVENTION

The present invention relates to a readily water-soluble ingestible form of ketoprofen formed by the reaction of ketoprofen with any edible weak base to yield a palatable, stable, safe solution for mass medication.

BACKGROUND OF THE INVENTION

Ketoprofen (Trade Name Orudis) is a known anti-inflammatory agent and one of the substituted propionic acids that inhibits prostaglandin-endoperoxide synthase. Propionic acid derivates are used in the treatment of rheumatoid arthritis, osteoarthritis, ankylosing spondylitis, and acute gouty arthritis. They are useful as analgesics, for acute tendinitis and bursitis, and for primary dysmenorrhea. In addition, they are very effective analgesics to relieve postpartum pain, and following oral, ophthalmic, or other types of surgery.

Clinical studies indicate that the propionic acid derivatives are comparable to aspirin for the control of the signs and symptoms or rheumatoid arthritis—there is a reduction in joint swelling, pain, and duration of morning stiffness. By objective measurements, strength, mobility, and stamina are improved. In general, the intensity of untoward effects is less than that associated with the ingestion of indomethacin or high doses of aspirin. However, aspirin is less expensive than most of the proprionic derivatives for those who can tolerate it.

Adverse effects include gastrointestinal complaints including nausea, vomiting, epigastric pain, reactivation of peptic ulcer, and other disturbances are common to all members of this group. CNS-related effects, such as dizziness, drowsiness, headache, and fatigue, also may occur. Drug interactions are not many, but since these drugs are very highly protein-bound, competition for binding sites could present a problem with oral anticoagulants or other highly protein-bound drugs. Toxicity is related primarily to the gastrointestinal tract, where ulceration and bleeding can be a problem.

Other members of the propionic acid derivative family include ibuprofen, naproxen, flurbiprofen, fenoprofen, and oxaprozin. The pharmacodynamics properties of the propionic acid derivatives do not differ significantly. All are effective cyclooxygenase inhibitors, although there is considerable variation in their potency. All of these agents alter platelet function and prolong bleeding time, and it should be assumed that any patient who is intolerant of aspirin also may suffer a severe reaction after administration of one of these drugs. Some of the propionic acid derivatives have prominent inhibitory effects on leukocyte function; naproxen is particularly potent in this regard. All are effective antiinflammatory agents in various experimental animal models of inflammation. All have useful antiinflammatory, analgesic, and antipyretic activities in human beings. Although all of these compounds can cause gastrointestinal side effects in patients, these are usually less severe than with aspirin.

Although it is a cyclooxygenase inhibitor, ketoprofen is believed to stabilize lysosomal membranes and may antagonize the actions of bradykinin. Ketoprofen has the general formula

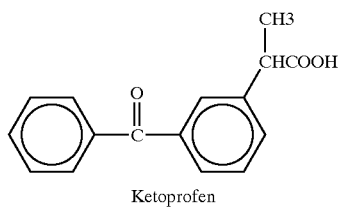

Ketoprofen

In humans, ketoprofen is rapidly absorbed after oral administration and maximal concentrations in plasma are achieved within 1 to 2 hours; food reduces the rate but not the extent of absorption. Ketoprofen, however, is distributed unevenly in body water. The drug is extensively bound to plasma proteins (99%) and it has a half-life in plasma of about 2 hours; slightly longer half-lives are observed in elderly subjects. The plasma half-life may vary between 1 and 35 hours; the causes of this variability are unknown. Ketoprofen is conjugated with glucuronic acid in the liver and the conjugate is excreted in the urine. Patients with impaired renal function eliminate the drug more slowly.

The claimed invention consists of forming a stable solution of ketoprofen in water for use in mass medicating animals and the addition of a flavoring agent to increase palatability. Current products on the market are given by injection and create significant problems if used for mass medication of farm animals (e.g., swine, cattle, horses, sheep, chickens, and goats) or for ongoing medication of small animals (e.g., dogs and cats). For example, injecting ketoprofen is time consuming and costly, especially with large numbers of animals involved. It is also potentially hazardous to the animal because a needle can break off in the animal and/or create an infective injection site. Feed even a farmyard animal, let alone a wildlife species, with tablets is minimally a taxing chore.

The claimed invention, a stable liquid form of ketoprofen, reduces concerns about the injection site, reduces the stress on the animal, allows for continuous medication over time at lower doses, and induces a steady state of drug in the animal's system. These advantages of the present invention reduce the potential for adverse affects on the animal. Such advantages also decreases the clearance time from removal of the drug to total body elimination due to the lack of the injection site.

The ability to administer ketoprofen in a non-invasive manner allows for the treatment of large groups of animals and for easier long-term treatment of individual animals with chronic disease. This formulation should prove beneficial in any condition where acute or chronic inflammation is involved where a desire to not give injections or pastes or pills is beneficial.

Although a number of references teach the use of ketoprofen, the ketoprofen compound itself is used with suitable organic and inorganic bases or oily solutions.

U.S. Pat. No. 6,069,172 (Bertini) describes a new use of the enantiomer (R)-ketoprofen and its salts with suitable organic and inorganic bases in the therapy of neutrophil-dependent diseases and phlogistic processes in a patient, and pharmaceutical preparations containing such compounds and useful for oral, parenteral or topical administration.

U.S. Pat. No. 5,665,384 (Courteille) describes stable, pharmaceutical ketoprofen salts for oral admininstration in oily solutions to avoid direct contact of acid forms of ketoprofen with the gastric or duodenal mucus membranes.

Sodium, arginine, lysine and/or N-methylglucamine salts of ketoprofen are disclosed in solutions of polyoxyethyenatide vegetable oil, castor oil, esters of fatty acids and/or polyols. These oily solutions of ketoprofen may be administered orally in capsule form.

Still other references describe the anlagesic and antipyretic activity of related agents or in some cases ketoprofen, without providing a stable, liquid form of administration.

Scand. J. Rheumatology, Suppl. 14: 33–44 (1976) describes the main pharmacological properties of ketoprofen, especially its anti-inflammatory, analgesic and antipyretic activity. Ketoprofen possesses the typical pharmacological properties of non-steroidal anti-inflammatory agents, i.e., anti-inflammatory, analgesic and antipyretic activity, as well as antibradykinin activity and ability to inhibit prostaglandin synthesis.

Bull. Soc.Vet.Prat.de France, 7/90, T. 74, No.7, p. 377 describes the use of ketoprophene as analgesic therapy in the treatment of equine colic (administered intravenously). A dosage of 2 mg per kg or 2 mL of 10% Ketoprofen solution per 100 kg was used.

Equine Vet. J. 19(1), 60–66 (1987) "Use of a novel non-steroidal anti-inflammatory drug in the horse" describes the use of a novel oral phenylpyrazoline anti-inflammatory agent (BW540C). An acute inflammatory reaction was generated by injecting carrageenin solution into subcutaneously-implanted tissue-cages lined with fibrovascular granulation tissue. BW540C inhibited platelet cyclooxygenase for 24 h but the reductions in exudates elcosanoid concentrations were less pronounced.

There is a need for stable liquid forms of ketoprofen that can be orally administered (i.e., ingested) via an animal's drinking water without rejection by the animal because of the bad taste imparted by the liquid ketoprofen. Such a palatable form of ketoprofen allows large scale dosage-controlled treatment of animals with the antibiotic.

SUMMARY OF THE INVENTION

The present invention comprises a stable, palatable solution of ketoprofen in water for use in mass medicating animals. Any edible weak base such as sodium bicarbonate may be used with ketoprofen in a ratio of 10 to 1 in order to completely and rapidly solubilize the ketoprofen in cold water and produce a palatable, stable, safe solution for mass medication.

DESCRIPTION OF THE PREFERRED EMBODIMENTS

The invention consists of forming a stable solution of Ketoprofen in water for use in mass medicating animals and the addition of a flavoring and sweetening agent to increase palatability.

First, any edible weak base such as sodium bicarbonate may be added to ketoprofen in a ratio of 10 to 1 in order to completely and rapidly solubilize the Ketoprofen in cold water and produce a palatable, stable, safe solution for mass medication.

A dose of 1 to 2 mg/kg provides effective relief of viral induced inflammatory processes and fevers. This allows livestock to continue eating and drinking normally and reduces the incidence of secondary diseases and the need to treat with antibiotics.

Second, flavoring or sweetening agents may be added to increase palatability of the end solution. Any of the following agents may be used: cyclohexyl-sulfamic acid, saccharin (o-benzosulfimide), and Aspartame (i.e., L-Aspartyl-L-phenylalanine methyl ester) sold as Nutrasweet® artificial sweetener, and the like, in small amounts that are sufficient to enhance the palatability. If the animals would not be adversely affected by inclusion of sugar in the formation, then sugar can be used to sweeten the solution. In actual practice, the sweetener and the flavoring are added in amounts that overcome the taste of ketoprofen.

The ketoprofen solution of the present invention is effective for analgesic treatment of a livestock animal. Also, the ketoprofen solution is effective for the treatment of an animal for rheumatoid arthritis, osteoarthritis, ankylosing spondylitis, acute gouty arthritis, acute tendonitis, bursitis and primary dysmenorrhea. For the above treatments, an effective amount of the ketoprofen solution is administered to the animal.

The following examples serve to illustrate the many applications of the present invention and should not be considered as limiting by any means.

EXAMPLE 1

Two 1000 head Finishing Barn Sites experienced an outbreak of swine influenza. Both barns, which housed 150 pound finishing hogs, experienced the outbreak simultaneously. We used one barn as the treatment group and one as the control group. The treatment group was given 1 mg/pound of Ketoprofen for 3 days orally through the drinking water and the control group was given a placebo of Flavored Sodium Bicarbonate in the water. We observed the pigs, until they were marketed at 260 pounds 8 to 10 weeks after the outbreak. The results of the study included an average time to market for the treatment group of 9 days less than the control group. The morbidity at the time of the outbreak was 10 percent in the treatment group and 90 percent in the control group. The mortality was 5.2 percent in the control group and 2.1 percent in the treatment group. The controls required follow-up treatment with antibiotics two weeks after the outbreak and the treatment group did not require any mass medication with antibiotics.

EXAMPLE 2

A 500 head cattle feedlot experienced an outbreak of IBR (Infectious Bovine Rhinotracheitis) a very contagious viral respiratory disease in cattle. At the time of the outbreak we divided the group in half and treated ½ with 1 mg/pound of Ketoprofen orally and ½ were used as controls. The cattle were treated that same in all other respects including intranasal vaccination and antibiotic treatment as needed. The animals were followed for 4 weeks post treatment and were scored based on Clinical signs, Morbidity, Mortality, Weight gain and rate of recovery. The results were as follows:

| Group | Mortality | Morbidity | Weight Gain*** | Clinical Score* | Rectal Temp.**** | Rate of Recovery** |
|---|---|---|---|---|---|---|
| Treatment | 0% | 60% | 75.8# | 1.5 | 102.3 | 3 days |
| Controls | 2% | 92% | 31.5# | 3.5 | 104.8 | 11 days |

*Based on a scale of 1 to 5 (1 = No symptoms to 5 = Severe symptoms)
**Days until no signs of disease
***Average weight gain per animal during the 4-week period of the study
****Average Daily Rectal Temperature in 30 randomly selected animals from each group taken daily for the first 7 days of the trial.

The results show a substantial decrease in mortality and morbidity. The animals returned to eating within 24 hours of beginning the treatment in the treatment group and the controls were off feed from 3 to 14 days. This is why the weight gains were so different.

EXAMPLE 3

An equine client with a horse with chronic laminitis was using phenylbutazone to try to control the inflammation and pain associated with the disease. This product had to be given to the horse daily by the owner. We tried giving Ketoprofen in the water at 1 mg per pound for 2 weeks to measure acceptance and intake. The results were very good. The horse readily drank the water with the medication and was less painful then when on the previous treatment.

EXAMPLE 4

A swine client with a 10,000 head nursery was experiencing severe mortality due to a PRRS (Porcine Respiratory and Reproductive Syndrome) Virus outbreak. They had used antibiotics with only partial success and were seeing mortalities as high as 30 percent in the group. We divided the barn into 2 groups and began treatment at the first signs of disease with the treatment group getting Ketoprofen orally for 7 days along with the same treatments as the controls for other therapy. The results were substantially reduced mortality 7% Treatment group versus 21% in the controls. We also saw less chronic pigs in the treatment group 3% versus 15% in the controls.

We claim:

1. A method for the analgesic treatment of a livestock animal comprising administering to said animal a pharmaceutically effective amount of a palatable aqueous solution said solution consisting essentially of ketoprofen, water, a flavoring agent, and an edible weak base; wherein said solution is administered to said animal in a non-encapsulated form.

2. The method of claim 1, wherein the base is selected from the group consisting of sodium bicarbonate, sodium chloride, potassium chloride, sodium sulfate, and potassium sulfate.

3. The method of claim 1 wherein the flavoring agent is selected from the group consisting of cyclohexyl-sulfamic acid, saccharin (o-benzosulfimide), Aspartame (i.e., L-Aspartyl-L-phenylalanine methyl ester), and sugar.

4. A method for the treatment of rheumatoid arthritis in an animal comprising administering to said animal a pharmaceutically effective amount of a palatable aqueous solution said solution consisting essentially of ketoprofen, water, a flavoring agent, and an edible weak base; wherein said solution is administered to said animal in a non-encapsulated form.

5. A method for the treatment of osteoarthritis in an animal comprising administering to said animal a pharmaceutically effective amount of a palatable aqueous solution said solution consisting essentially of ketoprofen, water, a flavoring agent, and an edible weak base; wherein said solution is administered to said animal in a non-encapsulated form.

6. A method for the treatment of ankylosing spondylitis in an animal comprising administering to said animal a pharmaceutically effective amount of a palatable aqueous solution said solution consisting essentially of ketoprofen, water, a flavoring agent, and an edible weak base; wherein said solution is administered to said animal in a non-encapsulated form.

7. A method for the treatment of acute gouty arthritis in an animal comprising administering to said animal a pharmaceutically effective amount of a palatable aqueous solution said solution consisting essentially of ketoprofen, water, a flavoring agent, and an edible weak base; wherein said solution is administered to said animal in a non-encapsulated form.

8. A method for the treatment of acute tendinitis in an animal comprising administering to said animal a pharmaceutically effective amount of a palatable aqueous solution said solution consisting essentially of ketoprofen, water, a flavoring agent, and an edible weak base; wherein said solution is administered to said animal in a non-encapsulated form.

9. A method for the treatment of bursitis in an animal comprising administering to said animal a pharmaceutically effective amount of a palatable aqueous solution said solution consisting essentially of ketoprofen, water, a flavoring agent, and an edible weak base; wherein said solution is administered to said animal in a non-encapsulated form.

10. A method for the treatment of primary dysmenorrhea in an animal comprising administering to said animal a pharmaceutically effective amount of a palatable aqueous solution said solution consisting essentially of ketoprofen, water, a flavoring agent, and an edible weak base: wherein said solution is administered to said animal in a non-encapsulated form.

11. The method of claim 1, wherein the weight ratio of weak base to ketoprofen as about 10:1.

12. A method for the analgesic treatment of a livestock animal comprising administering to said animal a pharmaceutically effective amount of a palatable aqueous solution said solution consisting essentially of ketoprofen, water, and an edible weak base; wherein said solution is administered to said animal in a non-encapsulated form.

13. The method of claim 12, wherein the weight ratio of weak base to ketoprofen is about 10:1.

* * * * *